US007682621B2

(12) United States Patent
Lamberty et al.

(10) Patent No.: US 7,682,621 B2
(45) Date of Patent: Mar. 23, 2010

(54) TRANSPARENT TOPICAL COSMETIC GEL HAVING COLORED FIBERS AND METHOD OF USING

(75) Inventors: Lisa Lamberty, Hawthorne, NJ (US); Irina Travkina, River Edge, NJ (US); Harold Pahlck, Waldwick, NJ (US)

(73) Assignee: Avon Products, Inc., New York, NY (US)

( * ) Notice: Subject to any disclaimer, the term of this patent is extended or adjusted under 35 U.S.C. 154(b) by 1517 days.

(21) Appl. No.: 10/891,843

(22) Filed: Jul. 15, 2004

(65) Prior Publication Data

US 2006/0013840 A1 Jan. 19, 2006

(51) Int. Cl.
*A61K 8/02* (2006.01)
*A61K 8/73* (2006.01)
*A61K 8/81* (2006.01)
*A61Q 5/06* (2006.01)

(52) U.S. Cl. ............... 424/401; 424/70.13; 424/70.15; 424/70.16

(58) Field of Classification Search ............... 424/401, 424/70.13, 70.16, 70.15
See application file for complete search history.

(56) References Cited

U.S. PATENT DOCUMENTS

| 5,601,812 | A | * | 2/1997 | Grossman | 424/70.15 |
| 5,711,943 | A | * | 1/1998 | Grossman | 424/70.15 |
| 6,342,237 | B1 | | 1/2002 | Bara | 424/401 |
| 6,503,521 | B1 | | 1/2003 | Atis et al. | 424/401 |
| 6,656,487 | B2 | | 12/2003 | Afriat et al. | 424/401 |
| 6,689,345 | B2 | * | 2/2004 | Jager Lezer | 424/64 |
| 2002/0028222 | A1 | | 3/2002 | Afriat | 424/401 |
| 2002/0098217 | A1 | * | 7/2002 | Piot et al. | 424/401 |
| 2004/0076649 | A1 | | 4/2004 | Blin et al. | 424/401 |
| 2004/0265257 | A1 | * | 12/2004 | Okuyama et al. | 424/70.7 |
| 2005/0169950 | A1 | * | 8/2005 | Delacour et al. | 424/401 |

FOREIGN PATENT DOCUMENTS

| JP | 03153613 | * | 7/1991 |
| JP | H3-153613 | * | 7/1991 |
| JP | 04-173718 | * | 6/1992 |
| WO | WO 02/41851 | | 5/2002 |

* cited by examiner

*Primary Examiner*—Shengjun Wang
*Assistant Examiner*—Umamaheswari Ramachandran
(74) *Attorney, Agent, or Firm*—Joan M. McGillycuddy; Charles J. Zeller; Anthony M. Santini

(57) ABSTRACT

There is provided a cosmetic gel. The gel has a multiplicity of colored fibers; one or more gellants; a film former different than the gellant if need for the gel to dry to a smooth film; and one or more liquid vehicles. The gel is substantially translucent, preferably transparent, and has a viscosity of about 100,000 cps to about 300,000 cps. The colored fibers are dispersed within the gel. The cosmetic gel dries to a dry, smooth film upon topical application. There is also a method for imparting color to the skin, hair, eyebrows, and eyelashes.

15 Claims, No Drawings

TRANSPARENT TOPICAL COSMETIC GEL HAVING COLORED FIBERS AND METHOD OF USING

BACKGROUND OF THE INVENTION

1. Field of the Invention

The present invention relates to a topical cosmetic gel useful for imparting color. The present invention further relates to a substantially transparent topical cosmetic gel useful for imparting color to the skin, hair, eyelashes, and eyebrows. The present invention still further relates to a method of topically imparting color.

2. Description of the Related Art

Mascaras are commonly employed by users to impart color and/or aesthetic effects to eyelashes. Conventional mascaras obtain their color or appearance from pigments or colorants dispersed within the base or vehicle of the mascara. The conventional mascaras typically take the form of an emulsion composition.

A drawback in using conventional mascaras is that while they typically impart color and/or aesthetic effects to eyelashes, they have limited effect in imparting a rich, lustrous appearance to or lengthening or thickening them. The prior art has attempted to address these limitations by incorporating white fibers into mascaras. However, white fibers have the aesthetic effect of whitening the lashes, which is undesirable. To offset this undesirable effect, pigmented mascara has to be applied to impart color and/or aesthetic effects. Alternatively, pigments are incorporated into the mascara to mask the white fibers.

It would be desirable to have a mascara that imparts a richer, more lustrous appearance than conventional mascaras. It would further be desirable to have a mascara that has the visual appearance of lengthening and thickening eyelashes while imparting a natural-looking color effect.

SUMMARY OF THE INVENTION

It is an object of the present invention to have a cosmetic composition that imparts a rich, lustrous appearance upon topical application to the skin, hair, eyebrows, or eyelashes.

It is further an object of the present invention to have a cosmetic composition that dries to a smooth, dry finish on the surface of the skin, hair, eyebrows, or eyelashes.

It is still further an object of the present invention to have a mascara that imparts rich, lustrous appearance to the eyelashes.

It is an object of the present invention to have a mascara that has the visual appearance effect of lengthening and thickening eyelashes.

According to these and other objects of the present invention, there is provided a cosmetic gel. The gel has a multiplicity of colored fibers, one or more gellants, one or more film formers different than the gellant if needed for the gel to dry to a smooth film, and one or more liquid vehicles. The gel is substantially transparent and has a viscosity of about 100,000 cps to about 300,000 cps. The colored fibers are dispersed within the gel. The cosmetic gel dries to a dry, smooth film upon topical application.

According to these and other objects of the present invention, there is a method for imparting color to the skin, hair, eyebrows, or eyelashes. A cosmetic gel as described above is topically applied to the skin, hair, eyebrows, or eyelashes.

DETAILED DESCRIPTION OF THE INVENTION

It was surprisingly found that an at least substantially transparent cosmetic gel could be formulated to topically impart color to the skin, hair, eyebrows, or eyelashes. It was further surprisingly found that that such a cosmetic gel could be formulated as a mascara, lip gloss/covering or browliner/definer.

The cosmetic gel of the present invention is substantially transparent. A gel is substantially transparent if the colored fibers dispersed therein are generally visible to the naked eye at a depth of at least 10 millimeters into the gel and preferably to a depth of at least 25 millimeters into the gel. Substantially transparent gels can be inclusive of both transparent gels and translucent gels. Preferably, the gel is transparent.

The gel gets its color in whole or in part from the presence of colored fibers dispersed therein. The fibers themselves have the visual appearance of being colored. The fibers can have an intrinsic color, e.g., the fibers can be dyed to have a uniform colored appearance throughout (outside and inside) the fibers, or be surface-treated or coated to take a certain color. The fibers are substantially insoluble in the cosmetic gel, including in the solvent(s). The fibers may be of a uniform color or be multicolored. If desired, the fibers may have patterned colors or take a patterned appearance. The colored fibers are a color other than white.

The fibers can be short or long, hollow or solid, individual or organized, such as, for example, bundles, clumps, and braids. The fibers can be of any shape. For example, circular and polygonal cross-sections, such as square, rectangular; hexagonal, and octagonal, are possible. The fibers can take any geometry lengthwise, such as straight, flat, curly, or spiral. The ends of the fibers can take any known shape, such as blunt, uneven, irregular, or wedge-like.

Suitable fibers typically have lengths of about 0.001 mm to about 10 mm, more typically about 0.1 mm to about 5 mm, and most typically about 0.5 mm to about 2.5 mm. The weight of the fibers per unit length of the fibers is typically less than 75 decitex, preferably less than about 50 decitex, and most preferably, especially in a mascara product, less than about 40 decitex. The term "dexitex" means unit weight in grams per 10,000 meters of fiber.

Suitable fibers include any of those known in the art, such as those derived from synthetic, natural, or mineral materials. The fibers may be of organic or inorganic materials. Suitable fibers include, but are not limited to, those derived from the following: silk; cotton; wool; flax; cellulose; rayon; wood; plants; algae; polyamides, such as nylon 6 and nylon 6,6; viscose; acetate; rayon acetate; acrylic polymers, such as polymethyl methacrylate and poly(2-hydroxyethyl methacrylate); polyolefins, such as polyethylene and polypropylene; glass; silica; carbon, such as graphite; polytetrafluoroethylene; insoluble collagen; polyesters; polyvinyl chloride; polyvinylidene chloride; polyvinyl alcohol; polyacrylonitrile; chitosan; polyurethane; and combinations thereof. Preferred fibers are those of nylon 6.

The fibers are visible in the cosmetic gel and are present in an amount sufficient to achieve their intended purpose when topically applied to the hair, eyelash, eyebrow, or skin substrates. The colored fibers may be present in such amount as to provide a visual appearance of color to the cosmetic gel while maintaining a substantially transparent appearance in the cosmetic gel. The fibers typically are present in an amount about 0.1 wt % to about 30 wt %, more typically about 0.2 wt % to about 5 wt %, and most typically about 0.5 wt % to about 2.5 wt % based on the total weight of the cosmetic gel.

The cosmetic gel has a gellant present in an amount sufficient to provide a gel structure, physical consistency, and adjustment of viscosity. The gel may be resilient/non-flowable or flowable. The viscosity ranges from about 100,000 cps to about 300,000 cps and preferably about 120,000 cps to about 250,000 cps. The gellant is typically present in an amount about 0.1 wt % to about 20 wt %, more typically about 0.2 wt % to wt %, and most typically about 0.4 wt % to about 0.8 wt % based on the total weight of the cosmetic gel.

The one or more gellants may be any known in the art including, but not limited to, the following: water-soluble cellulose polymers, such as hydroxyethylcellulose, methylcellulose, hydroxypropylmethylcellulose, and hydroxypropylcellulose; guar gums; quaternized guar gums; nonionic guar gums; xanthan gums; carob gums; scleroglucan gums; gellan gums; rhamsan gums; karaya gums; alginates; maltodextrin; starches; hyaluronic acid and salts thereof; clays, such as montmorillonites, hectorites and laponites; acrylates copolymer, crosslinked polyacrylic acid polymers, such as the "Carbopol" polymers of B.F. Goodrich; polyglyceryl (meth)acrylate polymers; polyvinylpyrrolidone; polyvinyl alcohol; crosslinked acrylamide polymers and copolymers; crosslinked methacryloyloxyethyltrimethylammonium chloride homopolymers; associative polymers, such as associative polyurethanes; and combinations thereof. Preferred gellants are crosslinked polyacrylic acid polymers. Gellants may or may not be film forming. Gellants that are also film forming (in addition to gelling) are preferred. If no film-forming gellants are present in the gel composition, then addition of one or more film formers is necessary.

The cosmetic gel leaves a dry, smooth film upon topical application to the surface of the skin, hair, eyebrows, or eyelashes upon drying or evaporation of any volatiles, including the solvent, from the gel. The film should exhibit good adhesion to the keratinous fibers and/or to the skin and should be elastic and not tacky so that it helps to adhere fibers to the lashes but not cause lashes to stick to each other. Many conventional gellants are known to form films suitable in the practice of the methods of the present invention. In the event that the one or more gellants do not have such film forming properties, or if the gellant is not present in an amount sufficient to provide a suitable film, one or more film formers are incorporated. The one or more film formers will be different than the one or more gellants.

Film formers may be water soluble/dispersible or oil soluble/dispersible. Film formers may be hydrophilic or hydrophobic depending on the solvent system in the cosmetic gel. Suitable film formers include, but are not limited to, the following: one or more acrylate copolymers such as acrylate/octylacrylamide copolymers and acrylate/vinyl acetate copolymers; ethylene/acrylic acid copolymer; polyacrylic acid; $C_1$ to $C_5$ alkyl galactomannan; adipic acid/diethylene glycol/glycerin crosspolymer; trimethylpentanediol/adipic acid copolymer; trimethylpentanediol/adipic acid/isononanoic acid; polyimides; alpha olefin/isopropyl maleate/maleic anhydride polymer; acrylates $C_{10}$ to $C_{30}$ alkyl acrylate crosspolymer; polyamides; diglycol/cyclohexanedimethanol/isophthalates/sulfoisophthalate copolymer; polyurethane resins; MQ resins such as trimethylsiloxysilicate; AT resins such as polymethylsilsesquioxane; rosin resins; hydrocarbon resins; isododecane/ethylene mixed copolymer; cycloalkyl methacrylate copolymer/isododecane; trimethyl polysiloxane octadecene/maleic anhydride copolymer; and mixtures of the foregoing. The polyurethane resins include Polyurethane-1, Polyurethane-2, Polyurethane-4, Polyurethane-5, and mixtures thereof. Additional film formers include those set forth in U.S. Pat. No. 5,916,541, which is incorporated herein by reference.

If one or more film formers is necessary, it is present in the cosmetic gel in an amount sufficient to provide a smooth, dry film upon application of the cosmetic gel to a substrate. Preferably, the one or more film formers would be present in an amount from about 0.1 wt % to about 20 wt %, more preferably in an amount from about 0.2 wt % to about 10 wt %, and most preferably from about 0.5 wt % to about 5 wt %.

The cosmetic gel of the present invention may be aqueous or non-aqueous. The gel has one or more liquid vehicles present in an amount sufficient to dissolve, solubilize, disperse, or suspend the various ingredients, including the one or more gellants and to provide a gel structure or form. An aqueous gel will have water as a vehicle or co-vehicle. A non-aqueous gel will have a hydrophobic vehicle(s). A non-aqueous gel may be oily or oil-based. Examples of aqueous gels include gels with water as the sole vehicle and gels having co-vehicles of water and one or more water-soluble (hydrophilic) or water-miscible vehicles, such as monohydric and polyhydric alcohols. Useful hydrophobic vehicles include, but are not limited to, volatile hydrocarbons, such as isododecane, and silicones, such as cyclomethicone. Cosmetic gels (aqueous or non-aqueous) preferably have about 10 wt % to about 99 wt %, more preferably about 60 wt % to about 95 wt %, and most preferably about 80 wt % to about 90 wt % solvent. Aqueous gels preferably have about 10 wt % to about 99 wt %, more preferably about 60 wt % to about 95 wt %, and most preferably about 80 wt % to about 90 wt % water.

Although the cosmetic gel of the present invention has a visual appearance of color provided by the colored fibers, the cosmetic gel optionally may have pigments and/or colorants therein.

The cosmetic gel optionally may include one or more of the following additional ingredients: anesthetics, anti-allergenics, antifungals, antimicrobials, anti-inflammatories, antiseptics, chelating agents, colorants, depigmenting agents, emollients, fragrances, humectants, lubricants, moisturizers, pharmaceutical agents, preservatives, skin protectants, skin penetration enhancers, stabilizers, surfactants, and vitamins apart from the colored fibers to provide additional color and/or visual effects.

The cosmetic gel is suited for use in a variety of cosmetic products. Such products include, but are not limited to, mascaras, eye shadow, eye liner, blush, foundation, lip gloss/covering. The cosmetic gel is particularly suited for functioning as a mascara or a lip gloss/covering. In the instance of the mascara, the colored fibers provide rich, lustrous color to the eyelashes and thicken and lengthen them. In the instance of the lip gloss/covering, the colored fibers provide rich, lustrous color to the lips, fill in crevices and lines at the surface of the lips, and provide a generally fuller appearance to the lips.

The compositions of the present invention can be made in accordance with conventional methods known in the art for making gel cosmetic products. In one method, a first aqueous premix of the gellant is prepared at slightly elevated temperature with sufficient agitation to ensure that all of the gellant is dissolved. A second premix is prepared by admixing the remaining components (excluding the colored fibers) under moderate temperature and shear followed by cooling to approximately the temperature of the gellant premix. The gellant premix is then incorporated with mixing into the second premix with stirring, and the combined mixture cooled to room temperature. The fibers are then dispersed into the gel with mixing. It will be within the knowledge of one skilled in the art and in the scope of the present invention to modify this method or to derive other gel-forming methods.

The following are examples of the present invention and are not to be construed as limiting. Unless otherwise indicated, all percentages and parts are by weight. All ingredients are "as is" unless other wise noted.

The following formulations were prepared in accordance with the method disclosed above.

EXAMPLE 1
Mascara Formulation

| | INGREDIENT | CONCENTRATION |
|---|---|---|
| PART A | DEMINERALIZED WATER | QS TO 100% |
| PART B | PRESERVATIVE | 0.4 GM |
| PART C | HYDROXYETHYLCELLULOSE | 1 GM |
| | PVP | 0.5 GM |
| PART D | BUTYLENE GLYCOL | 5 GM |
| | PROPYLENE GLYCOL | 2 GM |
| | DISODIUM EDTA | 0.2 GM |
| PART E | DEM. WATER | 2 GM |
| | TEA | 1.2 GM |
| PART F | DEM WATER | 50 GM |
| | CARBOPOL 940 | 0.7 GM |
| PART G | FIBERS[1] | 1.2 GM |

[1]Fiberlon 102BL405 black nylon fibers from Sensient

The components of Part F were mixed to form a first premix at slightly elevated temperature. Parts B thru E were admixed sequentially with Part A to form a second premix at moderate temperature. The second premix was cooled to about the temperature of the first premix, and the first premix was slowly added thereto. After cooling, the fibers were added under low shear to the mixture to form the final product formulation.

EXAMPLE 2
Mascara Formulation

| | INGREDIENT | CONCENTRATION |
|---|---|---|
| PART A | ISODODECANE | QS TO 100% |
| PART B | PRESERVATIVE | 0.4 GM |
| PART C | ISODODECANE/ETHYLENE MIX COPOLYMER | 40 GM |
| | ACRYLATES COPOLYMER | 10 GM |
| PART D | POLYISOBUTENE | 5 GM |
| | GLYCERYL ROSINATE | 5 GM |
| | ISOOCTAHEXACONTANE | 5 GM |
| PART F | FIBERS[1] | 2.5 GM |

[1]Fiberlon 102BL405 black nylon fibers from Sensient

The components of Part E were mixed to form a first premix at slightly elevated temperature. Parts B thru D were admixed sequentially with Part A to form a second premix at moderate temperature. The second premix was cooled to about the temperature of the first premix, and the first premix was slowly added thereto. After cooling the fibers were added under low shear to the mixture to form the final product formulation.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A substantially transparent mascara gel composition, comprising:
   one or more gellants selected from the group consisting of hydroxyethylcellulose, methylcellulose, hydroxypropylmethylcellulose, hydroxypropylcellulose; cetyl hydroxyethylcellulose; guar gums: quaternized guar gums; nonionic guar gums; xanthan gums; carob gums; scleroglucan gums; gellan gums; rhamsan gums; karaya gums; alginates; maltodextrin; starches; hyaluronic acid and salts thereof; clays, such as montmorillonites, hectorites and laponites; acrylates copolymer; crosslinked polyacrylic acid polymers; polyglyceryl (meth)acrylate polymers; polyvinylpyrrolidone; polyvinyl alcohol; crosslinked acrylamide polymers and copolymers; crosslinked methacryloyloxyethyltrimethylammonium chloride homopolymers; associative polymers, such as associative polyurethanes; and combinations thereof, in an amount sufficient to provide a substantially transparent mascara gel having a viscosity of about 100,000 cps to about 300,000 cps, wherein the gel dries to a smooth film upon topical application;
   a multiplicity of colored fibers selected from the group consisting of silk; cotton; wool; flax; cellulose; rayon; wood; plants; algae; polyamides, such as nylon 6 and nylon 6, 6; viscose; acetate; rayon acetate; acrylic polymers, such as polymethyl methacrylate and poly(2-hydroxyethyl methacrylate); polyolefins, such as polyethylene and polypropylene; glass; silica; carbon, such as graphite; polytetrafluoroethylene; insoluble collagen; polyesters; polyvinyl chloride; polyvinylidene chloride; polyvinyl alcohol; polyacrylonitrile; chitosan; polyurethane; and combinations thereof, dispersed within the mascara gel, wherein the fibers vary in length from about 0.001 mm to about 10 mm, and wherein the weight of the fibers per unit length of the fiber is less than about 75 decitex, such that the colored fibers provide a visual appearance of a color other than white to the mascara gel while maintaining a substantially transparent appearance in the mascara gel, wherein the colored fibers dispersed in the mascara gel are visible to the naked eye at a depth of at least 10 mm into the gel; and wherein the mascara has the visual appearance effect of lengthening and thickening eyelashes;
   one or more film formers selected from the group consisting of acrylate copolymers such as acrylate/octylacrylamide copolymers and acrylate/vinyl acetate copolymers; ethylene/acrylic acid copolymer; polyacrylic acid; $C_1$ to $C_5$ alkyl galactomannan; adipic acid/diethylene glycol/glycerin crosspolymer; trimethylpentanediol/adipic acid copolymer; polyimides; trimethylpentanediol/adipic acid/isononanoic acid; alpha olefin/isopropyl maleate/maleic anhydride polymer; acrylates $C_{10}$ to $C_{30}$ alkyl acrylate crosspolymer; diglycol/cyclohexane-dimethanol/isophthalates/sulfoisophthalate copolymer; polyurethane resins; MQ resins; AT resins; polyamides; rosin resins; hydrocarbon resins; isododecane/ethylene mixed copolymer; cycloalkyl methacrylate copolymer/isododecane; trimethyl polysiloxane octadecene/maleic anhydride copolymer and mixtures of the foregoing, different than the one or more gellants if needed for the mascara gel to dry to a smooth film; and
   one or more liquid vehicles.

2. The substantially transparent mascara gel composition of claim 1, wherein the gellant is present from about 0.1 wt % to about 20 wt %.

3. The substantially transparent mascara gel composition of claim 1, wherein the gel has the one or more film formers, and wherein the one or more film formers is present from about 0.1 wt % to about 20 wt %.

4. The substantially transparent mascara gel composition of claim 1, wherein the fibers are present from about 0.1 wt % to about 30 wt %.

5. The substantially transparent mascara gel composition of claim 1, wherein the gel has a viscosity of about 120,000 cps to about 250,000 cps.

6. The substantially transparent mascara gel composition of claim 1, wherein the gel is an aqueous gel.

7. The substantially transparent mascara gel composition of claim 1, wherein the gel is a non-aqueous gel.

8. A method for imparting color to the eyelashes, and the visual appearance effect of lengthening and thickening the eyelashes, comprising topically applying a substantially transparent mascara gel composition having one or more gellants selected from the group consisting of hydroxyethylcellulose, methylcellulose, hydroxypropylmethylcellulose, hydroxypropylcellulose; cetyl hydroxyethylcellulose; guar gums; quaternized guar gums; nonionic guar gums; xanthan gums; carob gums; scleroglucan gums; gellan gums; rhamsan gums; karaya gums; alginates; maltodextrin; starches; hyaluronic acid and salts thereof; clays, such as montmorillonites, hectorites and laponites; acrylates copolymer; crosslinked polyacrylic acid polymers; polyglyceryl(meth)acrylate polymers; polyvinylpyrrolidone; polyvinyl alcohol; crosslinked acrylamide polymers and copolymers; crosslinked methacryloyloxyethyltrimethylammonium chloride homopolymers; associative polymers, such as associative polyurethanes; and combinations thereof, in an amount sufficient to provide a substantially transparent mascara gel having a viscosity of about 100,000 cps to about 300,000 cps, wherein the gel dries to a smooth film upon topical application;

incorporating a multiplicity of colored fibers selected from the group consisting of silk; cotton; wool; flax; cellulose; rayon; wood; plants; algae; polyamides, such as nylon 6 and nylon 6, 6; viscose; acetate; rayon acetate; acrylic polymers, such as polymethyl methacrylate and poly(2-hydroxyethyl methacrylate); polyolefins, such as polyethylene and polypropylene; glass; silica; carbon, such as graphite; polytetrafluoroethylene; insoluble collagen; polyesters; polyvinyl chloride; polyvinylidene chloride; polyvinyl alcohol; polyacrylonitrile; chitosan; polyurethane; and combinations thereof, dispersed within the mascara gel such that the colored fibers provide a visual appearance of a color other than white to the mascara gel while maintaining a substantially transparent appearance in the mascara gel, wherein the colored fibers dispersed therein are generally visible to the naked eye at a depth of at least 10 mm into the gel;

one or more film formers selected from the group consisting of acrylate copolymers such as acrylate/octylacrylamide copolymers and acrylate/vinyl acetate copolymers; ethylene/acrylic acid copolymer; polyacrylic acid; $C_1$ to $C_5$ alkyl galactomannan; adipic acid/diethylene glycol/glycerin crosspolymer; trimethylpentanediol/adipic acid copolymer; polyimides; trimethylpentanediol/adipic acid/isononanoic acid; alpha olefin/isopropyl maleate/maleic anhydride polymer; acrylates $C_{10}$ to $C_{30}$ alkyl acrylate crosspolymer; diglycol/cyclohexane-dimethanol/isophthalates/sulfoisophthalate copolymer; polyurethane resins; MQ resins; AT resins; polyamides; rosin resins; hydrocarbon resins; isododecane/ethylene mixed copolymer; cycloalkyl methacrylate copolymer/isododecane; trimethyl polysiloxane octadecene/maleic anhydride copolymer and mixtures of the foregoing, different than the one or more gellants if needed for the mascara gel to dry to a smooth film; and one or more liquid vehicles.

9. The method of claim 8, wherein the gellant is present from about 0.1 wt % to about 20 wt %.

10. The method of claim 8, wherein the substantially transparent mascara gel composition has the one or more film formers, and wherein the one or more film formers is present from about 0.1 wt % to about 20 wt %.

11. The method of claim 8, wherein the fibers are present from about 0.1 wt % to about 30 wt %.

12. The method of claim 8, wherein the gel has a viscosity of about 120,000 cps to about 250,000 cps.

13. The method of claim 8, wherein the gel is an aqueous gel.

14. The method of claim 8, wherein the gel is a non-aqueous gel.

15. The substantially transparent mascara gel composition of claim 8, wherein the colored fibers are nylon 6.

* * * * *